(12) United States Patent
Horn

(10) Patent No.: US 10,118,466 B1
(45) Date of Patent: Nov. 6, 2018

(54) SCENTED PASTY WAX DELIVERY SYSTEM AND METHOD AND COMPOSITION

(71) Applicant: Meri Horn, Titusville, FL (US)

(72) Inventor: Meri Horn, Titusville, FL (US)

( * ) Notice: Subject to any disclaimer, the term of this patent is extended or adjusted under 35 U.S.C. 154(b) by 28 days.

(21) Appl. No.: 15/411,509

(22) Filed: Jan. 20, 2017

(51) Int. Cl.
| | |
|---|---|
| *B60H 3/00* | (2006.01) |
| *A61L 9/03* | (2006.01) |
| *B65D 35/08* | (2006.01) |
| *B65D 35/44* | (2006.01) |
| *B05B 11/04* | (2006.01) |

(52) U.S. Cl.
CPC .............. *B60H 3/0028* (2013.01); *A61L 9/03* (2013.01); *B05B 11/047* (2013.01); *B65D 35/08* (2013.01); *B65D 35/44* (2013.01); *A61L 2209/133* (2013.01); *A61L 2209/15* (2013.01); *B60H 2003/005* (2013.01); *B60H 2003/0057* (2013.01)

(58) Field of Classification Search
CPC ............ B60H 3/0028; B60H 2003/005; B60H 2003/0057; A61L 9/03; A61L 2209/113; B05B 11/047; B65D 35/08; B65D 35/44
USPC ........ 222/92, 3, 106, 107, 93; 422/123–125; 392/390, 391, 394, 386
See application file for complete search history.

(56) References Cited

U.S. PATENT DOCUMENTS

| | | | |
|---|---|---|---|
| 4,005,978 A | | 2/1977 | Calabretta et al. |
| 4,163,509 A | * | 8/1979 | Amneus .............. B65D 75/30 |
| | | | 137/846 |
| 5,052,554 A | * | 10/1991 | Leonard .............. A61C 9/0026 |
| | | | 206/219 |
| 5,497,913 A | * | 3/1996 | Baker .................. A61C 9/0026 |
| | | | 222/102 |
| 6,419,117 B1 | | 7/2002 | Bosch |
| 6,619,506 B2 | * | 9/2003 | Famiglietti ............ B65D 31/18 |
| | | | 222/103 |
| D485,341 S | * | 1/2004 | Wu ............................ D23/366 |

(Continued)

FOREIGN PATENT DOCUMENTS

DE 102009006193 A1 * 8/2010

OTHER PUBLICATIONS

Wilton Disposable Decorating Bags, Set of 12, Sur la table, retrieved from http://www.surlatable.com/product/PRO-560748//?affsrcid= AFF000 . . . , Jan. 4, 2017, 4 pages.

(Continued)

*Primary Examiner* — Lien Ngo
(74) *Attorney, Agent, or Firm* — Brian S. Steinberger; Law Offices of Brian S. Steinberger, P.A.

(57) ABSTRACT

Systems, devices, and methods for delivering selected amounts of scented, pasty wax mixtures for different applications of candle warmers, and compositions of scented, pasty wax mixtures which have extended fragrance lifespans. The warmers can include devices that melt the scented, pasty wax mixture, where the devices plug into vehicle accessory power outlets inside of vehicles or plug into wall power outlets or utilize solar power. The devices can include removable cartridges with or without sponges that can soak up the melting scented, pasty wax mixture to be disbursed throughout the space so that fragrances pass into the spaces. The scented, pasty wax mixture can include therapeutic essential oils to be dispersed throughout the spaces in high enough concentrations to provide the desired therapeutic availability.

18 Claims, 19 Drawing Sheets

(56) References Cited

U.S. PATENT DOCUMENTS

| | | | |
|---|---|---|---|
| 6,805,300 | B2 | 10/2004 | Munroe et al. |
| 7,046,919 | B2 * | 5/2006 | Shimizu .................... A61L 9/03 392/390 |
| 7,329,839 | B2 | 2/2008 | Palmer |
| 7,544,331 | B1 * | 6/2009 | Pettaway .................. A61L 9/03 392/386 |
| 7,641,078 | B2 | 1/2010 | Boumnso |
| 8,127,971 | B1 | 3/2012 | Chininis et al. |
| 8,551,195 | B2 | 10/2013 | Mitchell et al. |
| 8,752,730 | B2 | 6/2014 | Newman et al. |
| 8,878,102 | B2 * | 11/2014 | Juarez .................... H01R 33/22 219/209 |
| 2011/0068119 | A1 | 3/2011 | Wurster, Jr. |
| 2011/0127181 | A1 * | 6/2011 | Mitchell ................. A61L 9/012 206/277 |
| 2013/0277392 | A1 * | 10/2013 | Dominguez ....... B65D 75/5811 222/107 |
| 2015/0305089 | A1 * | 10/2015 | Belongia .............. H05B 3/0052 219/438 |

OTHER PUBLICATIONS

Wilton Disposable 16" Decorating Bag, 12 Count, Sur la table, retrieved from http://www.surlatable.com/product/PRO-1788025//?affsrcid=AFF00 . . . , Jan. 4, 2017, 3 pages.

Squeeze Scent, Angelic, retrieved from http://www.angeliccandlesonline.com/store/p2/Squeeze_Scent.html, Jan. 4, 2017, 2 pages.

Squeeze Scent, Angelic, retrieved from http://www.angeliccandlesonline.com/store/c1/Featured_Products.html, Oct. 17, 2016, 2 pages.

Parafflex 4627A, The International Group, Inc., Apr. 29, 2016, 2 pages.

4600 Series Products (Paraflex, Nochek, Astorlite) Petroleum Wax Blends, The International Group, Inc., Mar. 22, 1996, 6 pages.

IGI Candle Wax Blends, The International Group, Inc., retrieved from http://www.igiwax.com/by-industry/candleblends.html, Oct. 17, 2016, 3 pages.

IGI 4627 Comfort Blend Wax, Bitter Creek Candle Supply, Inc., Oct. 17, 2016 2 pages.

* cited by examiner

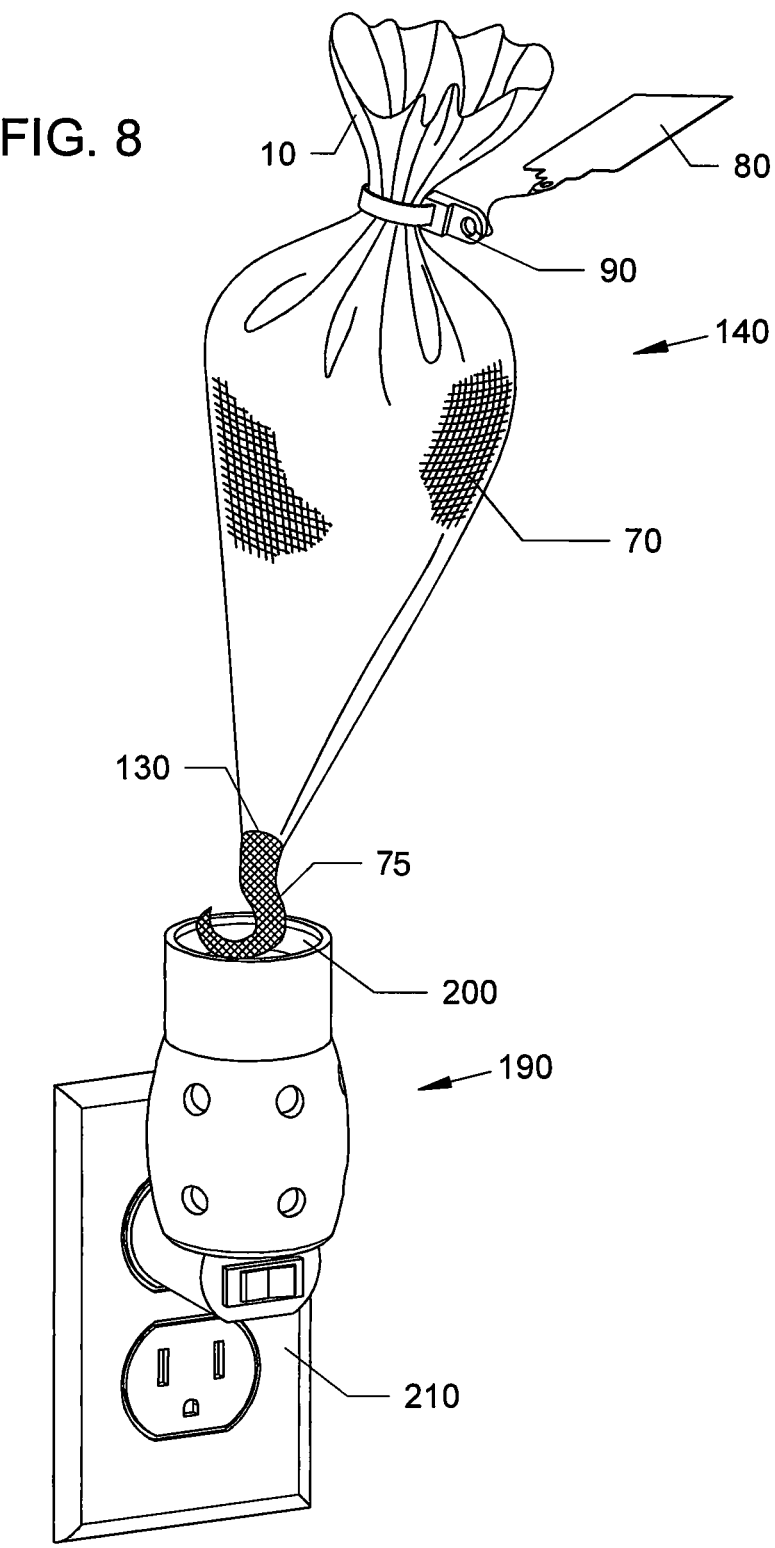

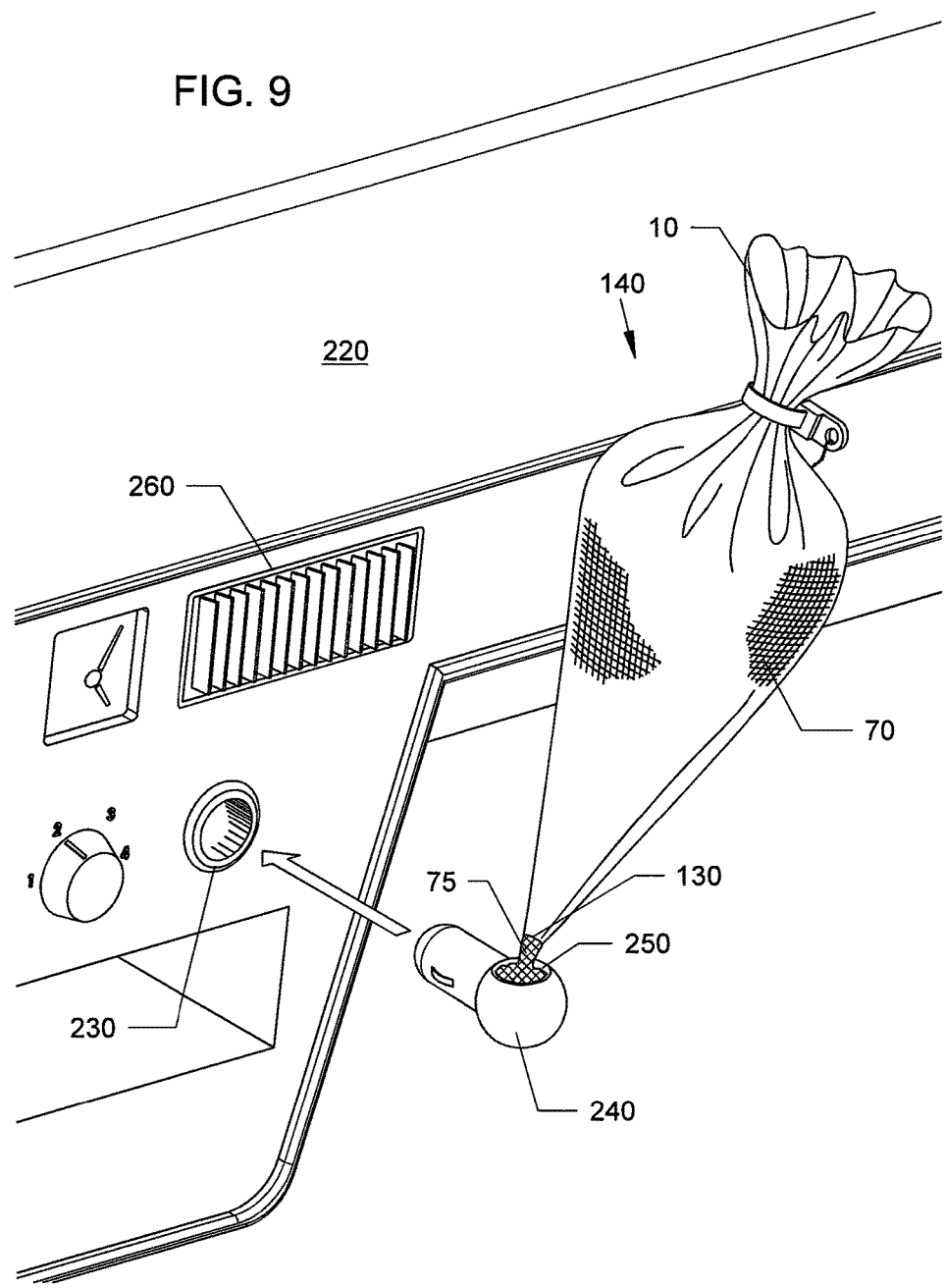

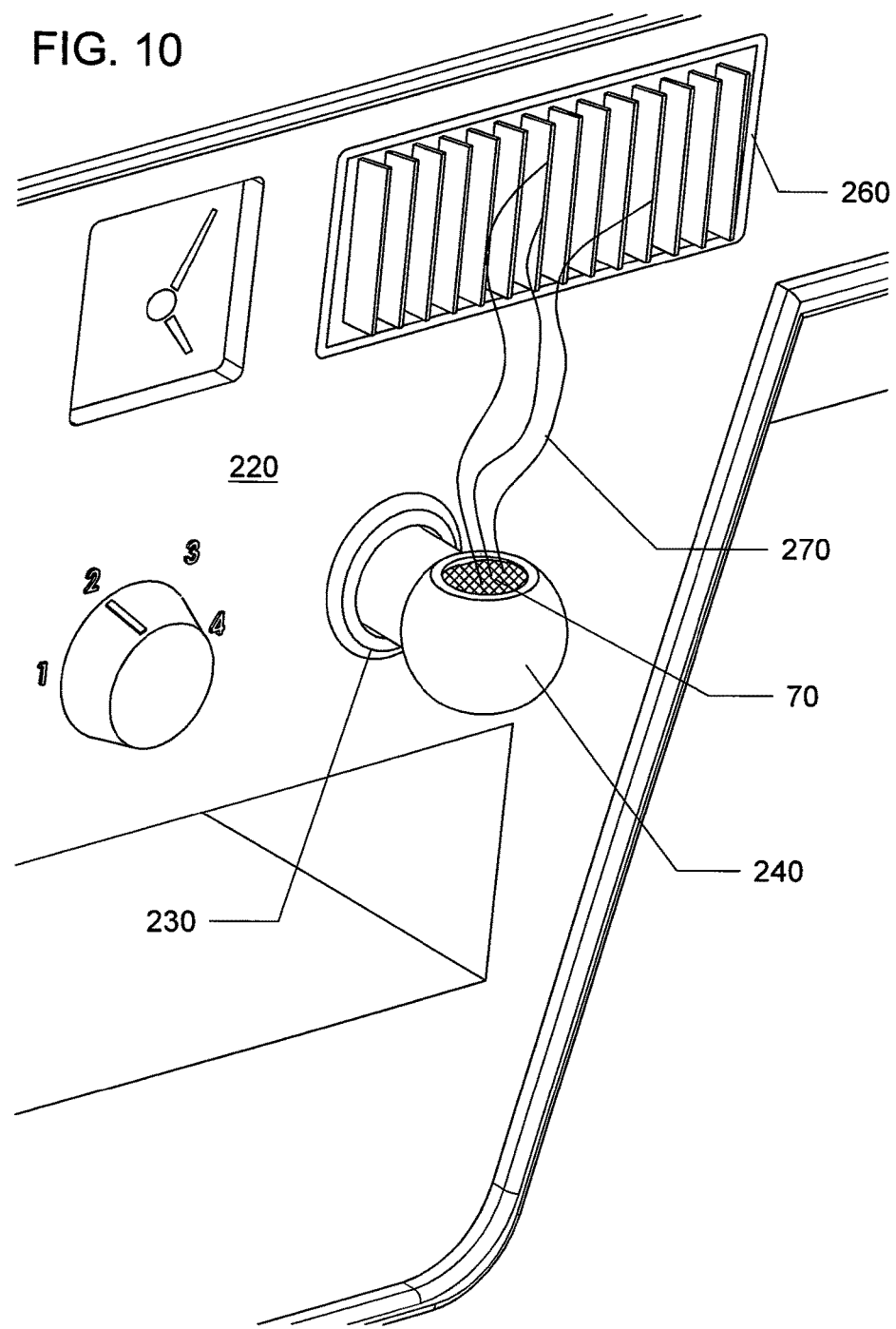

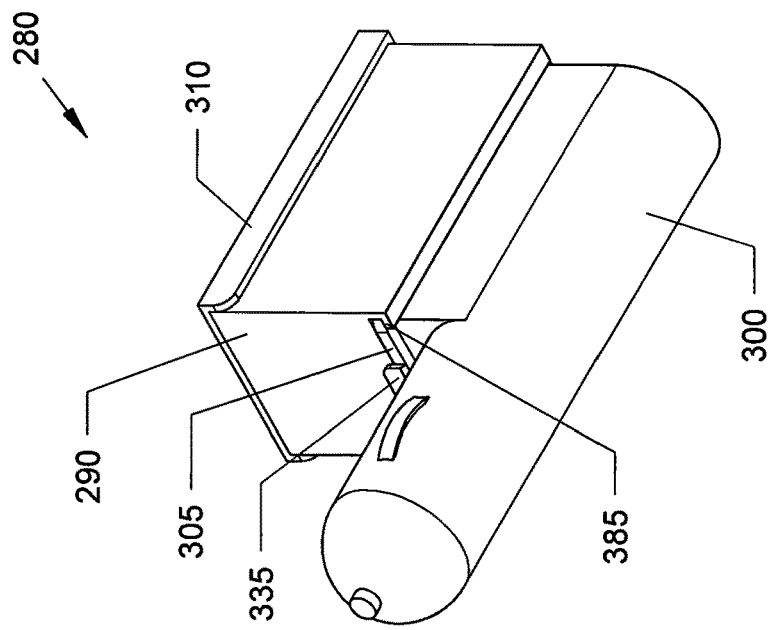
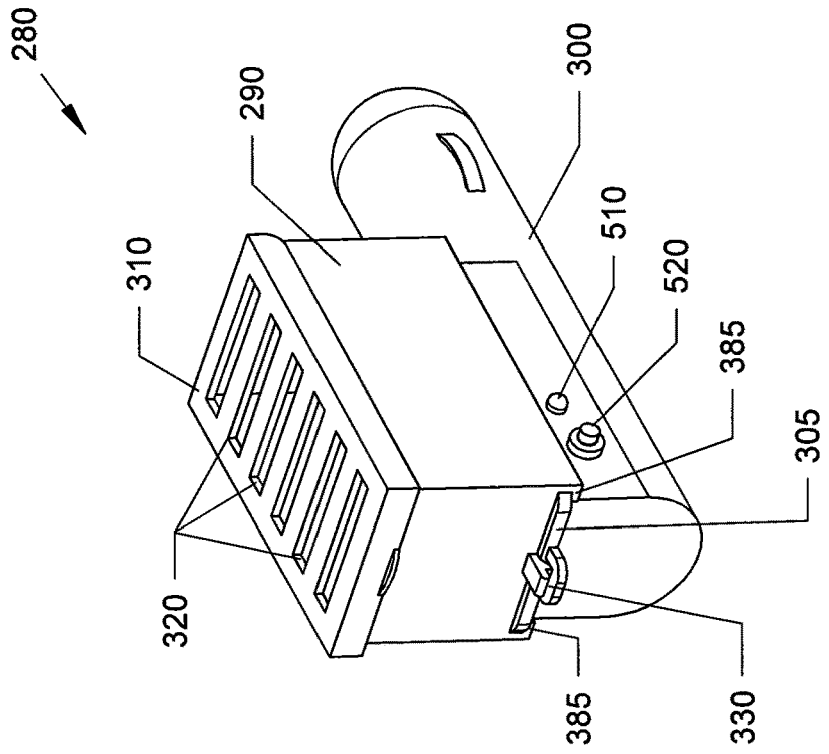

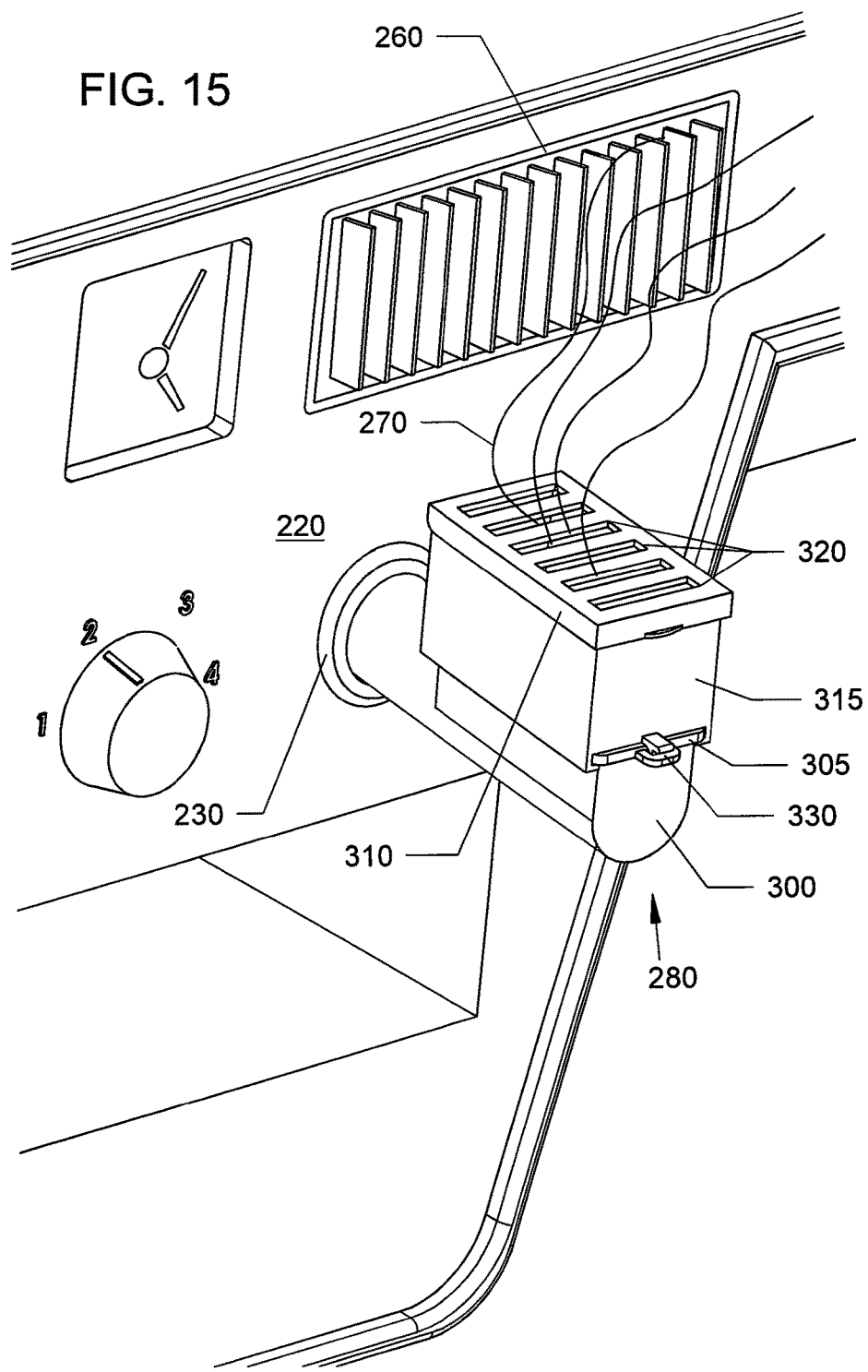

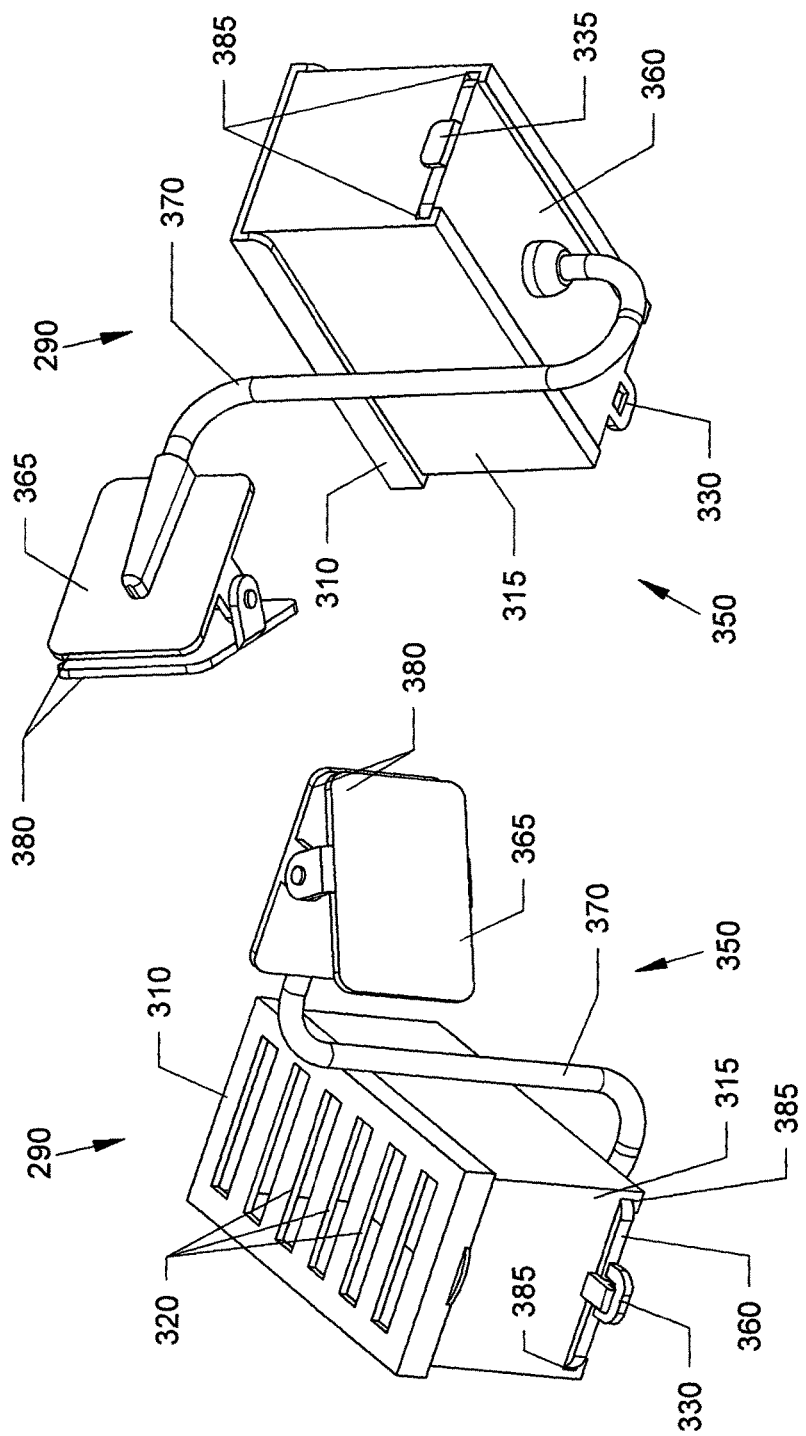

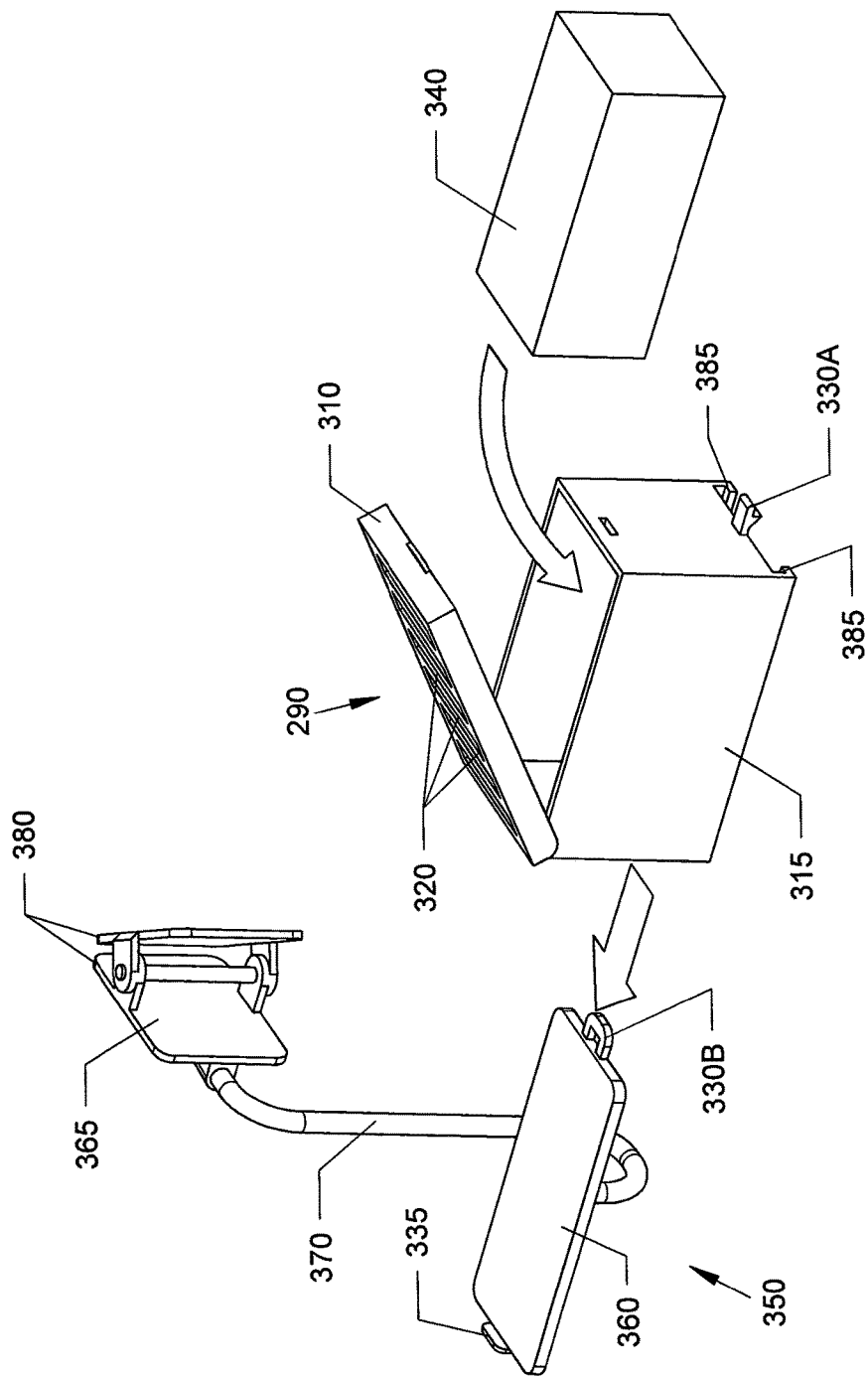

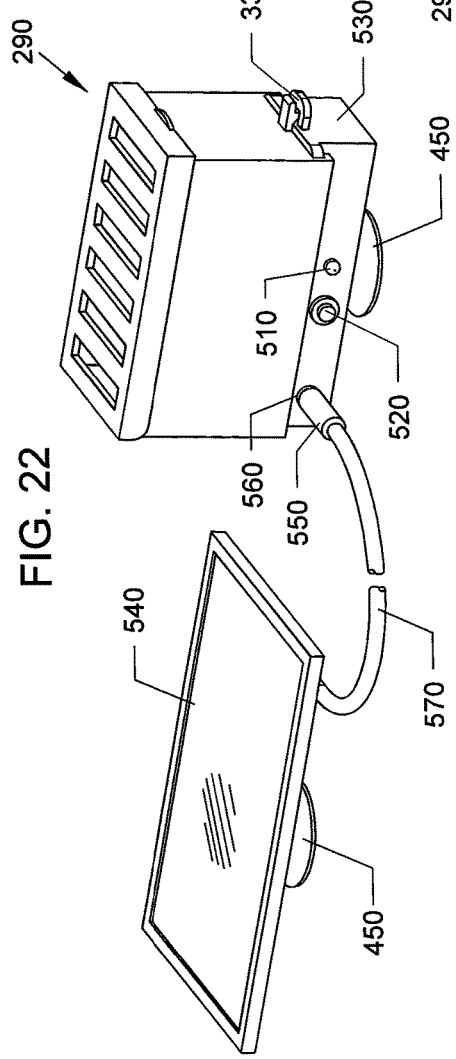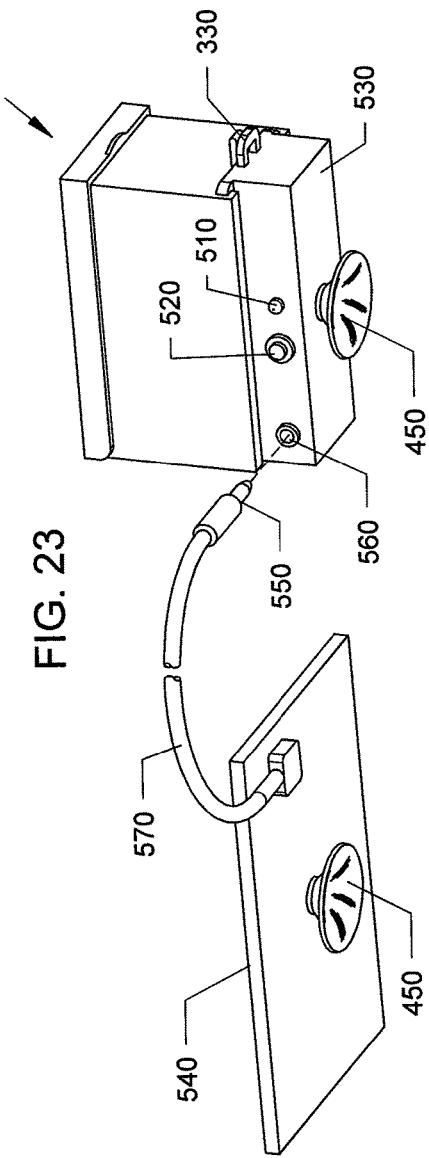

SCENTED PASTY WAX DELIVERY SYSTEM AND METHOD AND COMPOSITION

FIELD OF INVENTION

This invention relates to scented wax, and, in particular, to systems, devices, and methods for delivering selected amounts of scented, pasty wax mixtures for different applications in candle warmers, and compositions of scented, pasty wax mixtures which have extended fragrance lifespans, and compositions of scented, pasty wax mixtures with therapeutic aromatherapy properties.

BACKGROUND AND PRIOR ART

Candles and oil lamps have been in use since ancient times as a means of controllable, portable fire, consisting of a fuel and a wicking material to deliver the liquid fuel to the flame. They require either a container or jar of some sort to hold the liquid fuel or they must use fuel in a form that is at first solid and self-supporting, such as wax formed into a taper or a pillar, which then melts with the heat of the flame and, as before, the liquid fuel will wick its way up to the fire. In more recent years, the addition of scents and essential oils to the wax fuel, for the purpose of scenting the surrounding airspace as the scented fuel is consumed, has resulted in entirely new applications for the candle, and an entirely new industry of scenting one's home through various means. As the popularity of scenting the air in the home increased, it led to the popularity of scenting the air in vehicles, as well, although certainly not a feasible application for the candle.

From ambiance to pleasantly perfuming the surrounding area to aromatherapy, candles remain in high demand today for their variety of scents and ability to ease stress, although, true, therapeutic value aromatherapy is rarely possible with candles because the high temperature of the flame itself destroys many of the very molecules within the essential oils that provide the beneficial, therapeutic value.

As the popularity of scenting one's home and vehicle has grown, it has also become no longer necessary to use fire in the home for light and for heat, and many opt for ways to scent the home and certainly, vehicles, without the inherent danger of the flame. Candle warmers, such as but not limited to U.S. Pat. No. 7,329,839 to Palmer, which is incorporated by reference in its' entirety, have become popular in the home in this regard. They are used to heat and melt scented, solid wax cubes that contain no wick with which to feed a fire, but are instead melted to liquid form inside a dish, the heat causing the scent in the now liquid wax pool to evaporate and disperse into the surrounding air. The heat with which to melt the cube and disperse the scent, sometimes provided in the form of a light bulb, is applied to the dish of wax by the electric warmer.

The solid form of the wax cube limits the ability to select an amount of wax to melt. As one is restricted to the size of the cube, one is limited in the ability to select and control the strength of the scent released. The wax cube typically does not 'off gas' its aroma to an area of more than a few inches proximate when it is at room temperature in its un-melted, solid form. The cube, once melted, typically off gasses it's scent completely in a matter of hours and must be replaced. The required temperature to achieve scent dispersal by heat and the necessity of the liquid wax pool form to sufficiently release the scent inhibit one's ability to take favorite scents on the road, in their vehicles.

Thus, the need exists for solutions to the above problems with the prior art.

SUMMARY OF THE INVENTION

A primary objective of the present invention is to provide systems, devices, and methods for delivering selected amounts of scented, pasty wax mixtures for different applications of candle warmers, allowing for better control of the strength of scent released.

A secondary objective of the present invention is that, by virtue of the primary objective, selected amounts of two or more differently scented, pasty wax mixtures may be combined in any recipe for different applications of candle warmers, allowing for the creation of unique and custom scents not otherwise available.

A third objective of the present invention is to provide compositions of scented, pasty wax mixtures which have the ability to off gas enough scent to perfume one or more rooms while at room temperature.

A fourth objective of the present invention is to provide compositions of scented, pasty wax mixtures which have extended fragrance lifespans.

A fifth objective of the present invention is to provide compositions of essential oil infused, scented, pasty wax mixtures that are protected from degrading exposure to UV, that melt at a low enough temperature and off gas sufficiently for true, therapeutic value aromatherapy.

A sixth objective of the present invention is to provide compositions of scented, pasty wax mixtures with a device, delivery system and method that is fun to use.

A seventh objective of the present invention is to provide compositions of scented, pasty wax mixtures in a device that allows for endless artistic expression, providing infinite, unique display and gifting options not otherwise available.

An eighth objective of the present invention is to provide a 'portable' system, devices and method for use of scented, pasty wax mixtures in vehicles or other small, enclosed spaces (i.e., closets, cabinets, storage spaces, etc.) not normally suited for either flame or electrically heated, liquid wax scenting applications.

A cellulose open cell or natural sponge is placed in the portable cartridge, scented, pasty wax mixture is dispensed in a quantity partially or up to completely filling the cartridge with one or more scents, the cartridge is snapped closed. More scented, pasty wax may be added at any later time until complete sponge saturation is achieved. The cartridge can slide onto any heater base option, either electrically or solar powered, in either the home or a vehicle for melting or re-melting the scented, pasty wax mixture. Heating the mixture allows for greater scent dispersal, and as the liquid wax absorbs into the sponge and more surface area of wax is exposed to the air, the scent dispersal further increases. Pushing the button on any heater base option will activate heater at the preset temperature of approximately 135 to approximately 145 degrees F., the LED will illuminate indicating the heater is active. Heater and LED will turn off after approximately 20 minutes. Heater will melt scented, pasty wax to liquid form, liquid wax will be absorbed into the sponge. Scented, pasty wax will continue to release scent for days or more even when not heated.

The cartridge can be moved to an alternate base with or without the heater option for preferred scenting location. The cartridge may be moved to a closet, cabinet, tool box or storage container. The cartridge can be clipped to a car air vent for better dispersal of scent. The cartridge can be reheated numerous times to renew scent strength. Additional scented, pasty wax mixture can be added to cartridge until sponge is completely saturated. Wax will melt with the high internal temperature of a parked car in summer, renewing scent daily without need for heater. Scent within fully saturated sponge can last more than 6 weeks, sponge can be reheated or discarded and replaced with a new sponge at any time.

A system for dispensing the scented, pasty wax mixture, can include a flexible bag having a triangular shape with a wide base open end and a narrow closed tip end forming a funnel configuration, a supply of scented, pasty wax mixture for filling inside of the flexible bag, with the mixture being dispensed out of a narrow opening formed in the tip end of the flexible bag in a solid ribbon shape. The system can use a warmer for heating the pasty wax.

The flexible bag can be a clear transparent plastic, and can be a UV (ultraviolet) resistant plastic.

The system can include a tie for closing off the wide base open end of the flexible bag, or a clip for closing off the narrow tip end of the flexible bag after it is cut open.

The narrow, closed tip end of the flexible bag can include a plurality of cut lines on the exterior of the bag for allowing for different amounts of the scented, pasty wax mixture to be dispensed from the flexible bag.

The scented, pasty wax mixture can include a semi-viscous petroleum based wax which is squeezed out in a continuous ribbon shape from the dispensing bag.

The scented, pasty wax mixture can include a color and a fragrance. The mixture includes up to approximately 12% by weight of the fragrance and oils and up to approximately 1% color. The fragrance may or may not include essential oils for therapeutic aromatherapy.

The warmer can include a night light having a receptacle for receiving the dispensed scented, pasty wax mixture, the night light having a plug adapted for being plugged into an electrical outlet.

The warmer can include a removable cartridge for housing the receptacle, and an alternative mount or base for the cartridge with a clip for attaching the cartridge to an air vent grill.

The warmer can include a removable cartridge for housing the receptacle, and an alternative mount or base for attaching the cartridge to a surface, the mount being selected from one of hook and loop fasteners, or a suction cup, or any other mount, such as to a wall or shelf or hung from a hook or closet rod.

The warmer can include a vehicle accessory adapter having a receptacle for receiving the dispensed scented, pasty wax mixture, the vehicle accessory adapter having a plug adapted for being plugged into a vehicle accessory electrical outlet inside of a vehicle.

The warmer can include a solar cell heater option having a receptacle for receiving the dispensed, scented, pasty wax mixture, the heater having a jack that mates to the electrical plug from the solar cell, with the heater having multiple possible mounting styles.

The warmer can include a removable cartridge for housing the receptacle, and an alternative mount or base with a clip for attaching the cartridge to a vehicle air vent inside of a vehicle.

The warmer can include a removable cartridge for housing the receptacle, and an alternative mount or base for attaching the cartridge to a surface, the mount fastener being selected from one of hook and loop fasteners, or a suction cup, or any other mount, such as clipped to a visor or hung from the rearview mirror.

Further objectives and advantages of this invention will be apparent from the following detailed description of the presently preferred embodiments which are illustrated schematically in the accompanying drawings.

BRIEF DESCRIPTION OF THE FIGURES

FIG. 8 is a perspective view of the filled bag of the preceding figures dispensing scented, pasty wax mixture into night light style melter.

FIG. 9 is a perspective view of the filled bag of the preceding figures dispensing scented, pasty wax mixture into a car accessory melter.

FIG. 10 shows the car accessory melter of FIG. 9 plugged into car accessory receptacle and emitting scented wax aroma.

FIG. 11 is an upper perspective view of a cartridge based car accessory melter which can be plugged into a vehicle cigarette lighter. This embodiment would have a fixed temperature of approximately 135 to approximately 145 degrees F. and a timed, automatic shutoff.

FIG. 12 is a bottom perspective view of the car accessory of FIG. 11.

FIG. 15 is another view of the cartridge based melter of FIGS. 11-14 plugged into car accessory receptacle and emitting scented wax aroma.

FIG. 16 is a top perspective view of another embodiment of a clip-on style base cartridge holder. The cartridge in this embodiment is the same as the previous embodiment.

FIG. 17 is a bottom perspective view of clip-on style base cartridge holder of FIG. 16.

FIG. 18 is an exploded view of the clip-on style base cartridge holder of FIGS. 16-17.

FIG. 22 is a top perspective view of another embodiment of an alternative mount that can be powered by a solar panel with the panel and heating unit mountable to surfaces using suction cups.

FIG. 23 is a bottom perspective view of the embodiment of FIG. 22.

DESCRIPTION OF THE PREFERRED EMBODIMENTS

Figure 1:
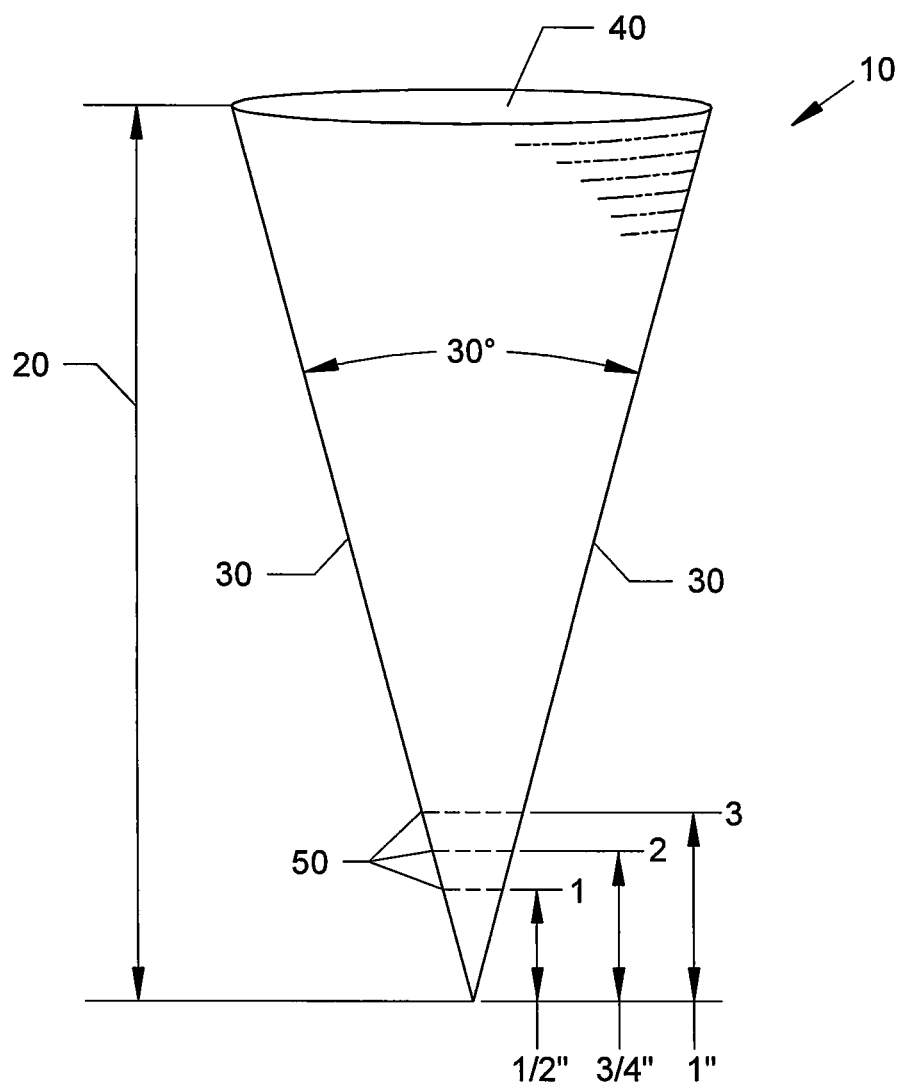
FIG. 1 is a front view of a dispense bag used in the invention.

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

In the Summary above and in the Detailed Description of Preferred Embodiments and in the accompanying drawings, reference is made to particular features (including method steps) of the invention. It is to be understood that the disclosure of the invention in this specification does not include all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

In this section, some embodiments of the invention will be described more fully with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will convey the scope of the invention to those skilled in the art. Like numbers refer to like elements throughout, and prime notation is used to indicate similar elements in alternative embodiments.

A list of components will now be described.
10 Dispense bag.
20 Variable bag length.
30 Sealed bag seams.
40 Open bag end.
50 Graduated cut lines for different dispense rates.
60 Dispense bag filled with scented, pasty wax mixture.
70 Scented, pasty wax mixture.
75 Ribbon of dispensed scented, pasty wax mixture.
80 I.D. Tag with string.
90 Zip tie with hole to close bag and to provide string anchor for I.D. Tag, for hanging product for display, and as attachment point for creative expression.
100 Bag tip pinched flat.
110 Scissors. Prior art.
120 Bag tip cut away at graduated line to dispense scented, pasty wax mixture.
130 Bag tip open.
140 Bag with scented, pasty wax mixture filled, tied, and tagged.
150 Table top style melter.
160 Power cord.
170 Fold in flattened, cut open bag tip to contain scented, pasty wax mixture.
180 Paper clip clamps fold.
190 Night light style wax melter.
200 Night light melter melting tray.
210 Power receptacle.
220 Car dashboard.
230 Accessory receptacle.
240 Car wax melter fits into accessory receptacle.
250 Melting tray for car wax melter.
260 Car air vent.
270 Melted, scented wax aroma.
280 Cartridge style car wax melter assembly.
290 Cartridge assembly, slides onto any style base.
300 Vehicle electric heater style melter base cartridge holder with fixed temperature heater and timed auto shut off.
305 Hot plate.
310 Cartridge lid.
315 Cartridge body.
320 Cartridge lid vents.
330A Cartridge assembly snap retains cartridge on any style base.
330B Snap receptacle on every style base assembly.
335 Cartridge stop.
340 Sponge.
350 Assembled cartridge on clip-on style base cartridge holder without solar heater melter option.
360 Clip-on style base without solar heater melter option.
365 Clamp.
370 Arm.
380 Clamp jaws.
385 Inwardly facing rails to slide onto sides of any style base.
390 Air vent vanes.
400 Assembled cartridge on basic style base cartridge holder without solar heater melter option.
410 Basic style base without solar heater melter option.
420 Hook and loop fasteners.
450 Suction cup(s).
510 LED (light emitting diode).
520 Push button on/off power switch.
530 Suction cup style base cartridge holder with solar heater melter option.
540 Solar panel.
550 RCA type plug.
560 RCA type jack.
570 Solar panel cable.

The invention can use a pasty wax that is a semi viscous petroleum derived wax, such as but not limited to Paraflex 4627A by the International Group, Inc., a natural beeswax, a soybean derived wax such as but not limited to GW464 by Golden Foods/Golden Brands, or any other pasty wax or wax type material or blend with a low melting point. The pasty wax can be distributed in a ribbon, from the novel disposable flexible bag to be described below, similar to a ribbon being dispensed from a toothpaste tube.

The inventors add color and a maximum of approximately 12% fragrance oil by weight. The larger amount of fragrance allows for a better and longer aroma effect from the dispensed scented, pasty wax mixture.

The colors can include any color, such as but not limited to red, pink, maroon, burgundy, purple, deep purple, lavender, midnight blue, blue, sky blue, pine, green, sage, yellow, orange, pumpkin, mahogany, brown, caramel, honey, beige, ivory, and variations, shades and tints thereof, as well as black and white and shades of grey, and the like.

Fragrances can include any type of smell, such as but not limited to different types of fruits and flavors, such as but not limited to black cherry, blood orange, raspberry sangria, blackberry sage, pineapple paradise, coconut lime, lavender chamomile, oakmoss and amber, baby powder, pine forest, black coffee, vanilla hazelnut, vanilla, chocolate, sweet pea, gingerbread, hazelnut coffee, Caribbean teakwood, island hibiscus, jasmine, gardenia, rose garden, clean cotton, love spell, pumpkin pie, peppermint and eucalyptus, white tea and berries, smoke and odor eliminator, frankincense and myrrh, nag champa, sunwashed linen, apples and maple bourbon, mulled cider and chestnuts, amaretto nog and the like.

Table 1 lists the components of a scented, pasty wax mixture that can be used.

TABLE 1

| Component | Broad Range | Narrow Range | Preferred Amount |
| --- | --- | --- | --- |
| Pasty wax, such as IGIs 4627A | approx. 87% to approx. 94% | approx. 87% to approx. 90% | approx. 88% |
| Fragrance Oils &/or Essential Oils | approx. 6% to approx. 13% | approx. 10% to approx. 13% | approx. 12% |
| Colors | less than approx. 1% | less than approx. 1% | less than approx. 1% |

Other types of wax can be used, such as but not limited to those described in U.S. Pat. No. 4,005,978 to Calabretta et al. and U.S. Pat. No. 8,551,195 to Mitchell et al., which are both incorporated by reference in their entirety.

Figure 2:
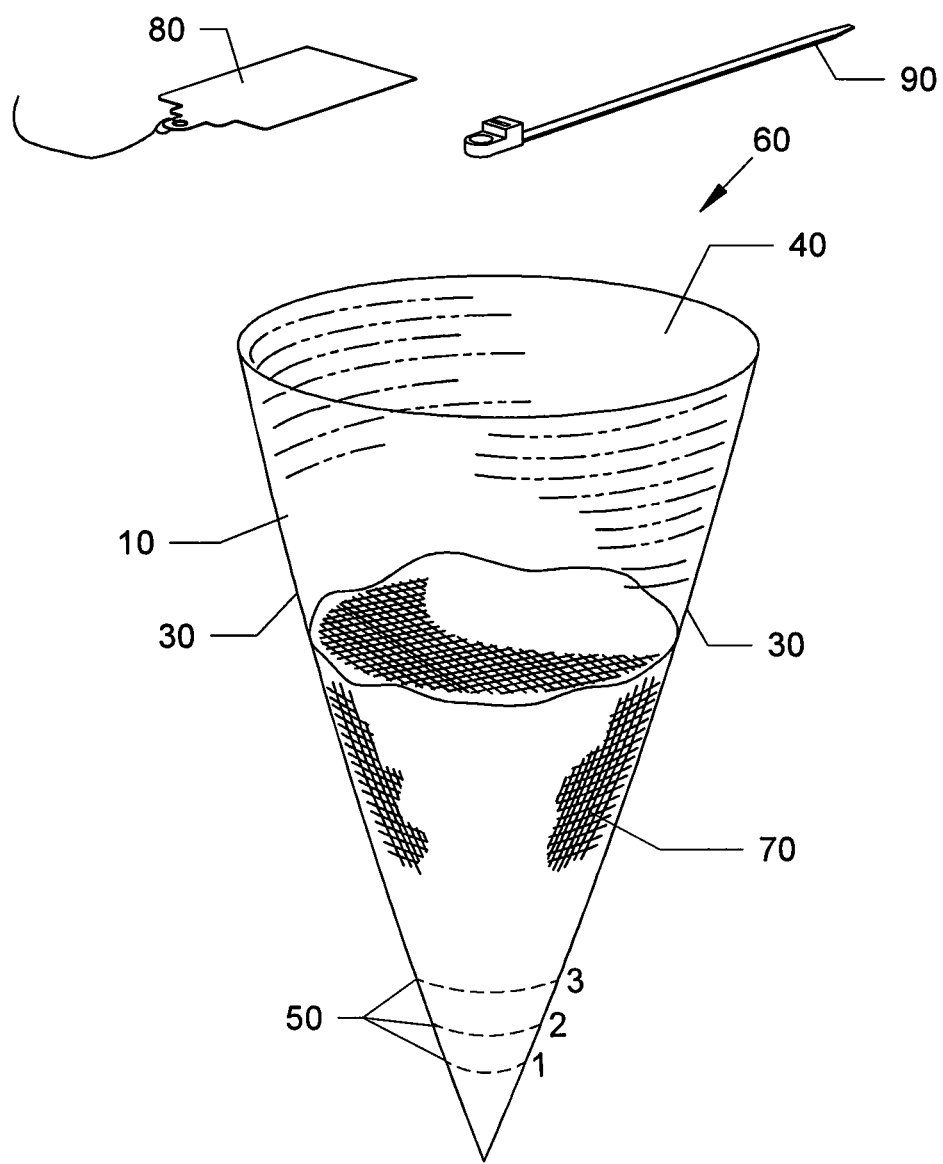
FIG. 2 is a perspective angled view of the dispense bag of FIG. 1 filled with scented, pasty wax mixture with a tag and a tie.
Figure 3:
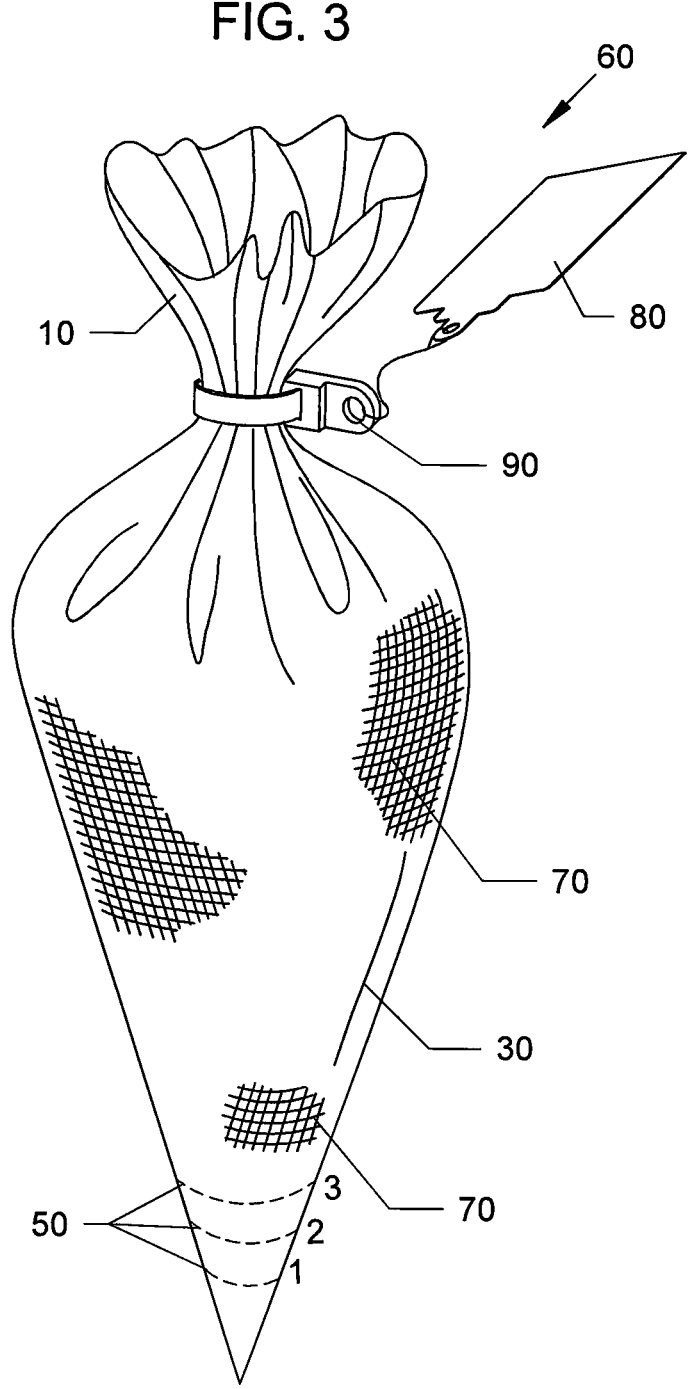
FIG. 3 is a side view of the dispense bag of FIG. 2 with the open end tied closed and the tag attached.
Figure 4:
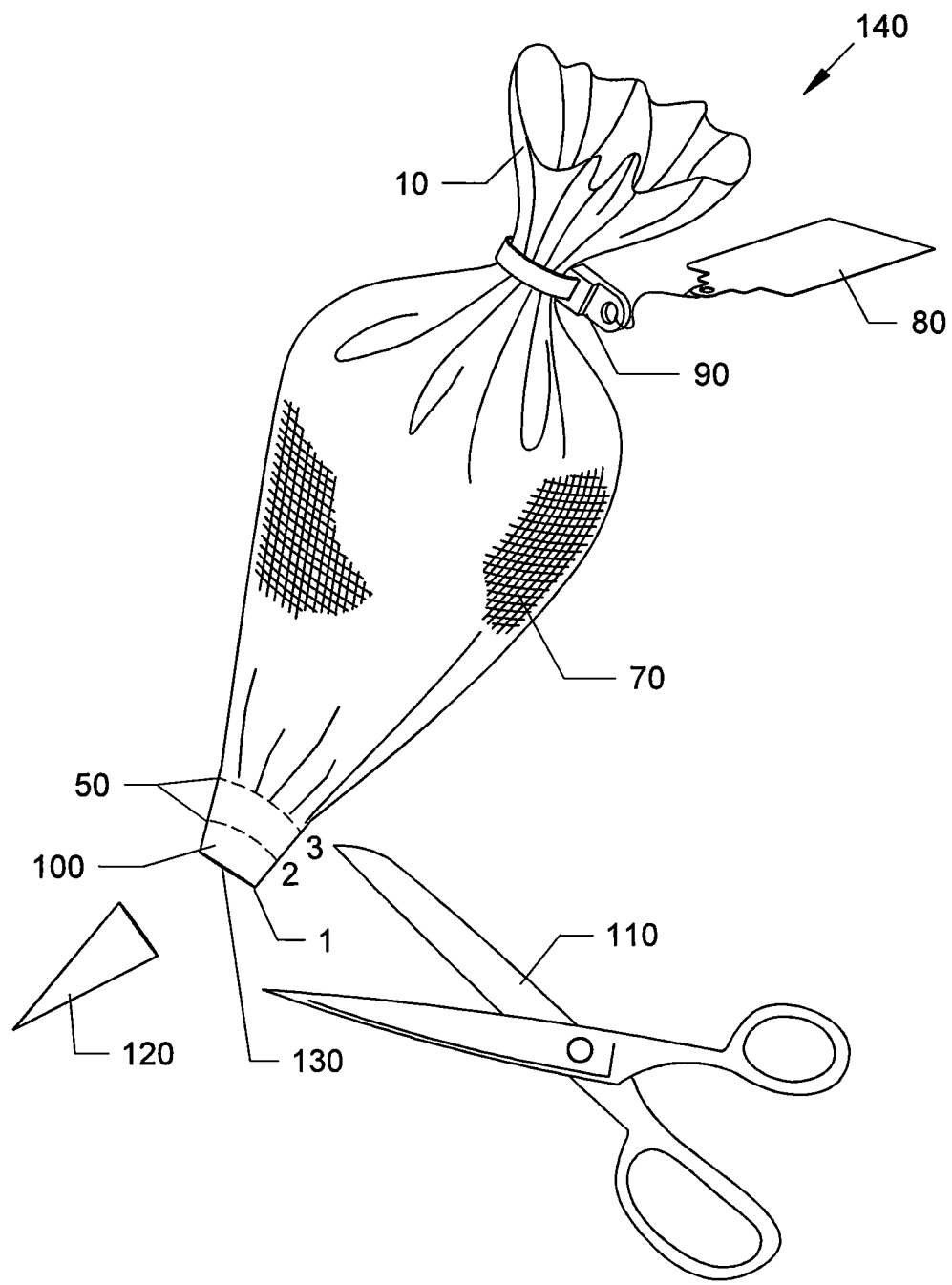
FIG. 4 is a perspective view of the filled bag of FIG. 3 with the tip end cut ready for the contents of the bag to be dispensed.

FIG. 1 is a front view of a dispense bag 10 used in the invention. FIG. 2 is a perspective angled view of the dispense bag 10 of FIG. 1 filled with scented, pasty wax mixture 70 with an ID (identification) tag 80 and a zip tie with hole 90. FIG. 3 is a side view of the filled dispense bag 10 of FIG. 2 tied closed with zip tie 90 and labeled with the attached ID (identification) tag 80. The tag 80 can be used to label the stored scented, pasty wax mixture, and include but not be limited to the type of fragrance, and the like. FIG. 4 is a perspective view of the filled dispense bag 10 of FIG. 2 tied by the zip tie 90 with tag 80, and the flattened tip end 120 cut off by a scissors 110 and ready for the contents 70 of the bag 10 to be dispensed from the tip opening 130. The bag 10 can be a clear transparent plastic bag, and/or a bag that is colored with the color of the wax to be used or any other color. The bag can be UV (ultra violet) resistant to preserve the efficacy of essential oils for therapeutic aromatherapy applications.

Referring to FIGS. 1-4, the dispensing bag 10 can include an open wide bag end 40 and closed narrow tip end 100 that can have a generally triangular configuration with seams 30, and to the tip end 100 forms a generally funnel and conical shape when the bag 10 is filled. The length of the bag 20 can be approximately 12 inches or approximately 16 inches or any other size as needed.

The inside of the bag 10 can be filled with a scented, pasty wax mixture 70 as in perspective view 60, that was previously described above.

The user can flatten the tip end 100, which can have a plurality of graduate cut lines 50, such as up to three or more cut lines. In a preferred embodiment, a bottom cut line can have a height from the tip of approximately ½ inch, a second cut line can have a height from the tip of approximately ¾ inch, and a third cut line can have a height from the tip of approximately 1 inch. The user can cut along one of the cut lines 50 with a scissors 110, or knife or razor to form a desired dispensing opening. With the cut lines 50 the user can control the amount of scented, pasty wax mixture 70 to be dispensed from the flexible bag 10.

Table 2 shows the amount of pasty wax product that can be dispensed from different cut line openings.

TABLE 2

| Snip Tip at Line | 1 | 2 | 3 |
| --- | --- | --- | --- |
| Width of Opening with Tip Flattened | 5/16" | 7/16" | 5/8" |
| Diameter of Ribbon | 3/16" | 5/16" | 7/16" |
| Length of Ribbon needed to equal ½ teaspoon | 4" | 2½" | 1½" |
| Length of Ribbon needed to equal 1 Cube | 16" | 10" | 6" |

Referring to FIGS. 1-4 and Table 2, a user dispensing a ribbon of scented, pasty wax mixture from the bag can apply approximately ½ a teaspoon of product which can provide at least approximately 8 hours of scent when being dispensed onto a warmer.

For wax warmers that use solid cubes of wax for warming, then 2 ounces can be equivalent to 6 cubes of use, hence, 6 uses. Here, 2 ounces can be equivalent to approximately 12 teaspoons, which can be equivalent to up to 24 uses.

Figure 5:
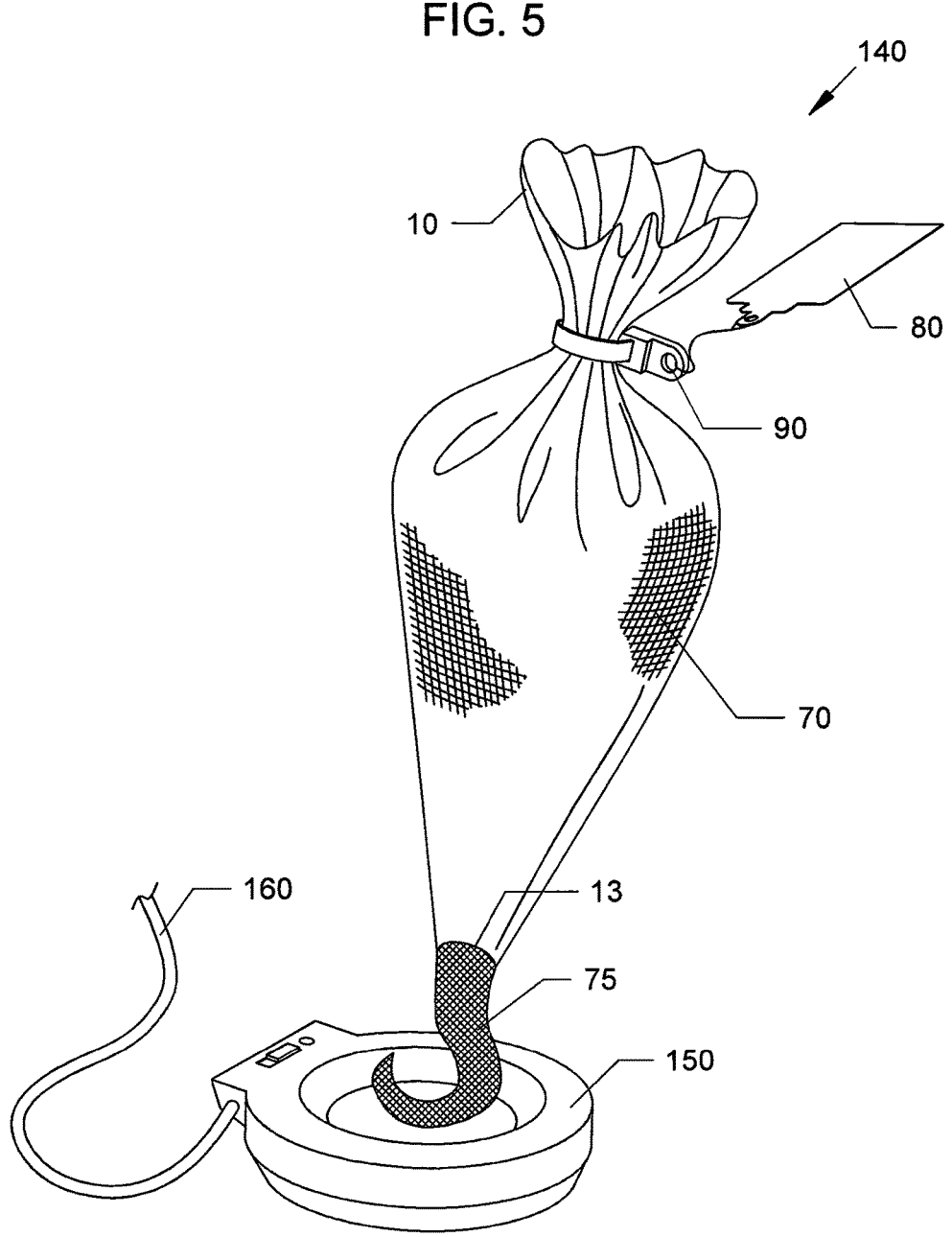
FIG. 5 shows the bag of FIG. 4 with cut tip dispensing scented, pasty wax mixture into table top melter.

FIG. 5 shows the bag 140 of FIG. 4 with cut tip opening 130 dispensing scented, pasty wax mixture as a ribbon 75 into table top melter 150 that can be plugged by a power cord 160 into a power outlet 210. The melter 150 can be a candle warmer, such as but not limited to U.S. Pat. No. 7,329,839 to Palmer, which is incorporated by reference in its' entirety. After a selected ribbon 75 of scented, pasty wax mixture is dispensed onto the warmer 150, it is turned on and melts the wax to release the desired fragrance effect into the atmosphere.

Figure 7:
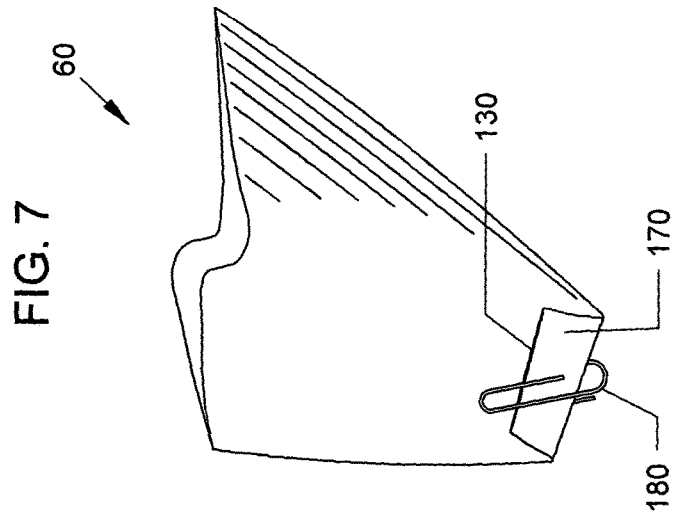
FIG. 7 shows the bag with folded tip of FIG. 6 with a clip securing the folded tip.
Figure 6:
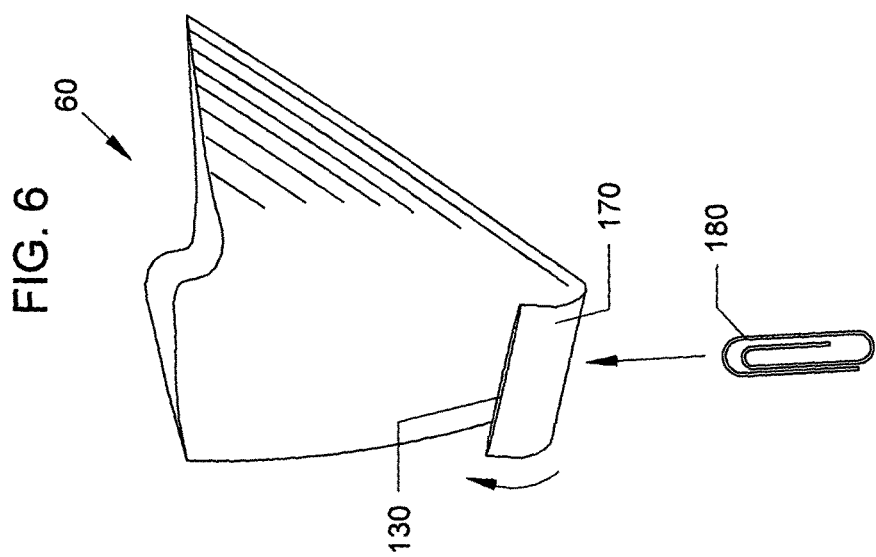
FIG. 6 is an enlarged view of the bag of the preceding figures with the tip pinched flat and folded.

FIG. 6 is an enlarged view of the bag 60 of the preceding figures with the flattened tip 170 folded. FIG. 7 shows the bag 60 with flattened, folded tip 170 of FIG. 6 and closed off with a clip 180 securing the flattened, folded tip 170.

FIG. 8 is a perspective view of the filled bag 140 of the preceding figures dispensing scented, pasty wax mixture as a ribbon 75 into a tray/receptacle 200 of a night light style melter 190 that can be plugged into an electrical outlet 210.

FIG. 9 is a perspective view of the filled bag 140 of the preceding figures dispensing a scented, pasty wax mixture ribbon 75 into a receptacle/tray 250 on a car accessory melter 240 that can be plugged into a cigarette lighter outlet (accessory receptacle) 230 inside of a vehicle. FIG. 10 shows the car accessory melter 240 of FIG. 9 plugged into car accessory receptacle 230 and emitting scented wax aroma 270. When the scented, pasty wax mixture 75 is being melted, the outcoming air from the vehicle air vent 260 under the dash 220 can further distribute the scented air 270 throughout the vehicle.

FIG. 11 is an upper perspective view of an assembled cartridge based car accessory melter 280 which can be plugged into a vehicle accessory receptacle 230. This embodiment would have fixed temperature and a timed, automatic cutoff.

The melter 300 can turn on by push-button switch 520. An indicator light emitting diode (LED) 510 comes on to signal the melter is heating. Temperature settings can be calibrated at 135 to 145 degrees F. for the scented, pasty wax mixture 70 being used. The melter 300 automatically turns off after approximately 15 or approximately 20 minutes, and the LED goes out when it is turned off.

FIG. 12 is a bottom perspective view of the assembled car accessory melter 280 of FIG. 11.

Figure 13:
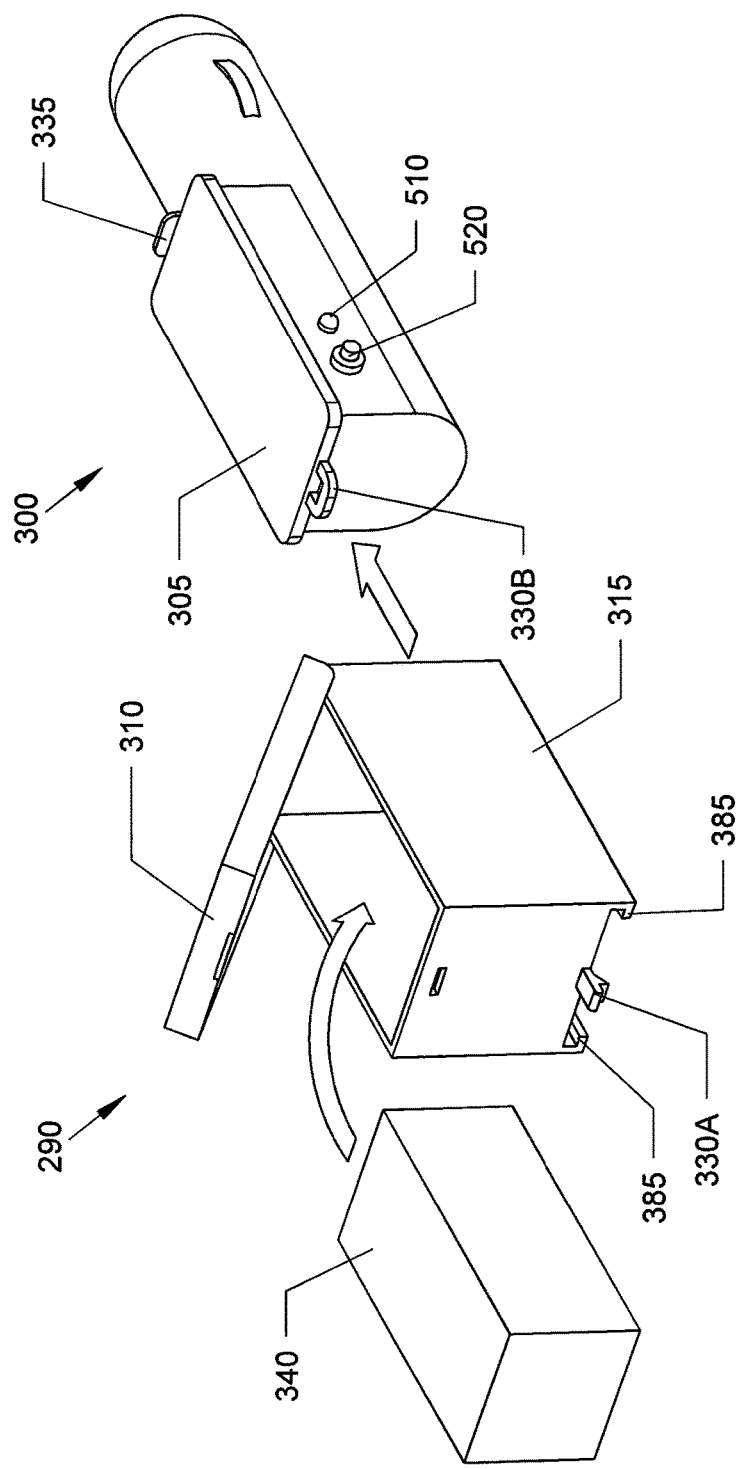
FIG. 13 is an exploded view of the car accessory of FIGS. 11 and 12.

FIG. 13 is an exploded view of the car accessory 280 of FIGS. 11-12.

Figure 14:
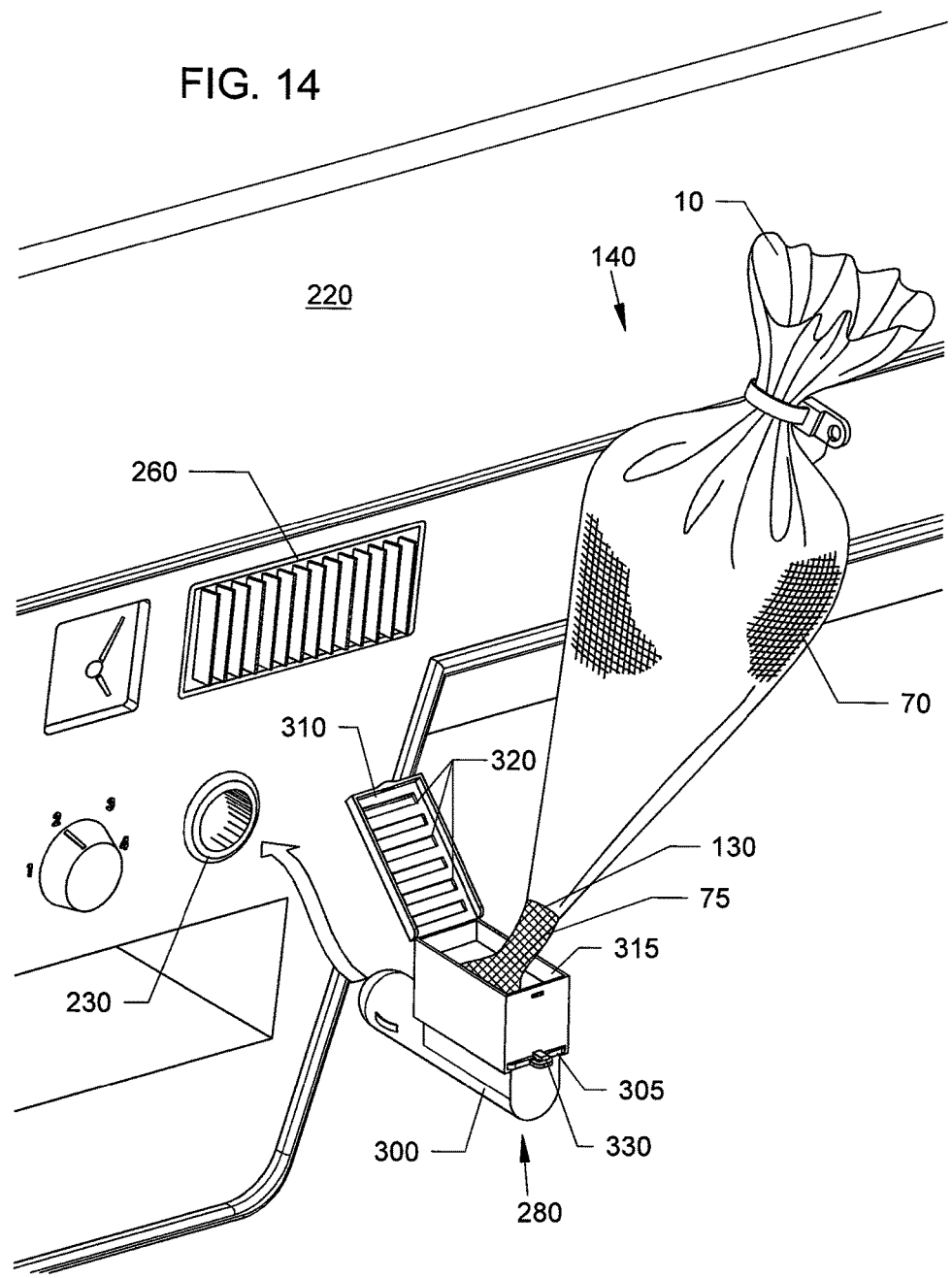
FIG. 14 is a perspective view of the car accessory of FIGS. 11-13 with cartridge lid open and bag dispensing scented, pasty wax mixture into cartridge onto top of sponge.

FIG. 14 is a perspective view of the car accessory assembly 280 of FIGS. 11-13 with cartridge lid 310 open and bag 140 dispensing scented, pasty wax mixture 75 into cartridge 315 onto top of sponge 340.

FIG. 15 is another view of the cartridge based melter assembly 280 of FIGS. 11-14 plugged into car accessory receptacle 230 and emitting scented wax aroma 270.

Referring to FIGS. 11-15, the cartridge based melter assembly 280 can include a cartridge 290 having a cartridge body(housing) 315 with a hinged lid 310 having vents 320 where a sponge 340 can be housed therein. The bottom of the housing 315 can have inwardly facing rails 385 that can slide onto side edges of a hot plate 305 which is on a melter base 300. A snap 330A on the bottom front end of the housing 315 can clip onto a snap receptacle 330B when the back of the housing 315 reaches a cartridge slide stop 335. The user can squeeze the bag 140 to dispense a ribbon 75 of scented, pasty wax mixture into the housing 315 and onto the sponge 340 inside of the housing 315.

The sponge 340 can include but is not limited to open cell foam material or cellulose or natural sponge.

The user places the sponge 340 inside of the housing 315 and then dispenses the ribbon 75 of the scented, pasty wax mixture on top of the sponge 340. The scented, pasty wax ribbon 75 melts when the cartridge melter assembly 280 is turned on.

The scent becomes "portable" when the scented, pasty wax mixture 75 melts directly into the sponge 340. When in a liquid form, the scented, pasty wax mixture 75 will become 'suspended' within the sponge 340 similar to water being suspended in a sponge, so it will not drip. And even when solid, the sponge structure allows significant surface area exposure of the scented, pasty wax mixture 75 which increases the already high fragrance output.

The user can turn on the cartridge based melter assembly 280 so that the scented, pasty wax ribbon 75 inside of the housing 315 starts to melt and the melted wax aroma 270 is dispensed by the vent outlet 260 throughout the inside of the vehicle.

FIG. 16 is a top perspective view of another embodiment of a clip-on style base cartridge holder assembly 350 without a solar heater option. The cartridge 290 in this embodiment is the same as the previous embodiment. FIG. 17 is a bottom perspective view of clip-on style base cartridge holder 350 of FIG. 16. FIG. 18 is an exploded view of the clip-on style base cartridge holder of FIGS. 16-17 with a clip-on style basic base 360 which functions as a cartridge support similar to the hot plate 305 but without the heater option.

As will be described below for other embodiments, the cartridge 315 with the melted scented, pasty wax mixture 75 can then be positioned in other locations, such as but not limited to being clipped to air conditioning vent, hung from mirror, and the like, for days of fragrance before being needed to be remelted to "refresh" fragrance output. Fragrance will last for weeks before exhausting all appreciable output, at which time sponge 340 will need replacement.

Figure 19:
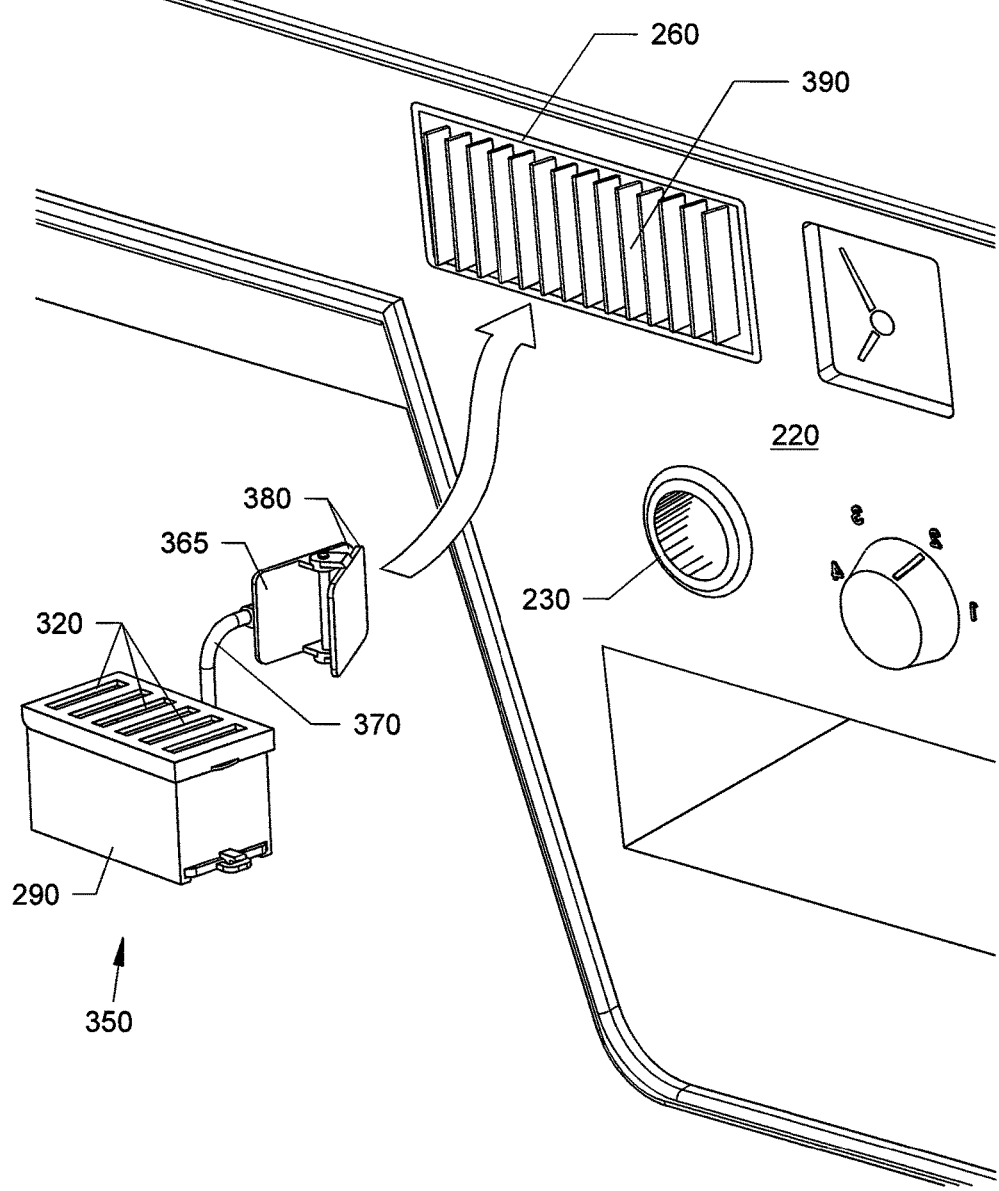
FIG. 19 is a perspective view of clip-on style base cartridge holder of FIGS. 16-18 ready to clip to a car vent vane.
Figure 20:
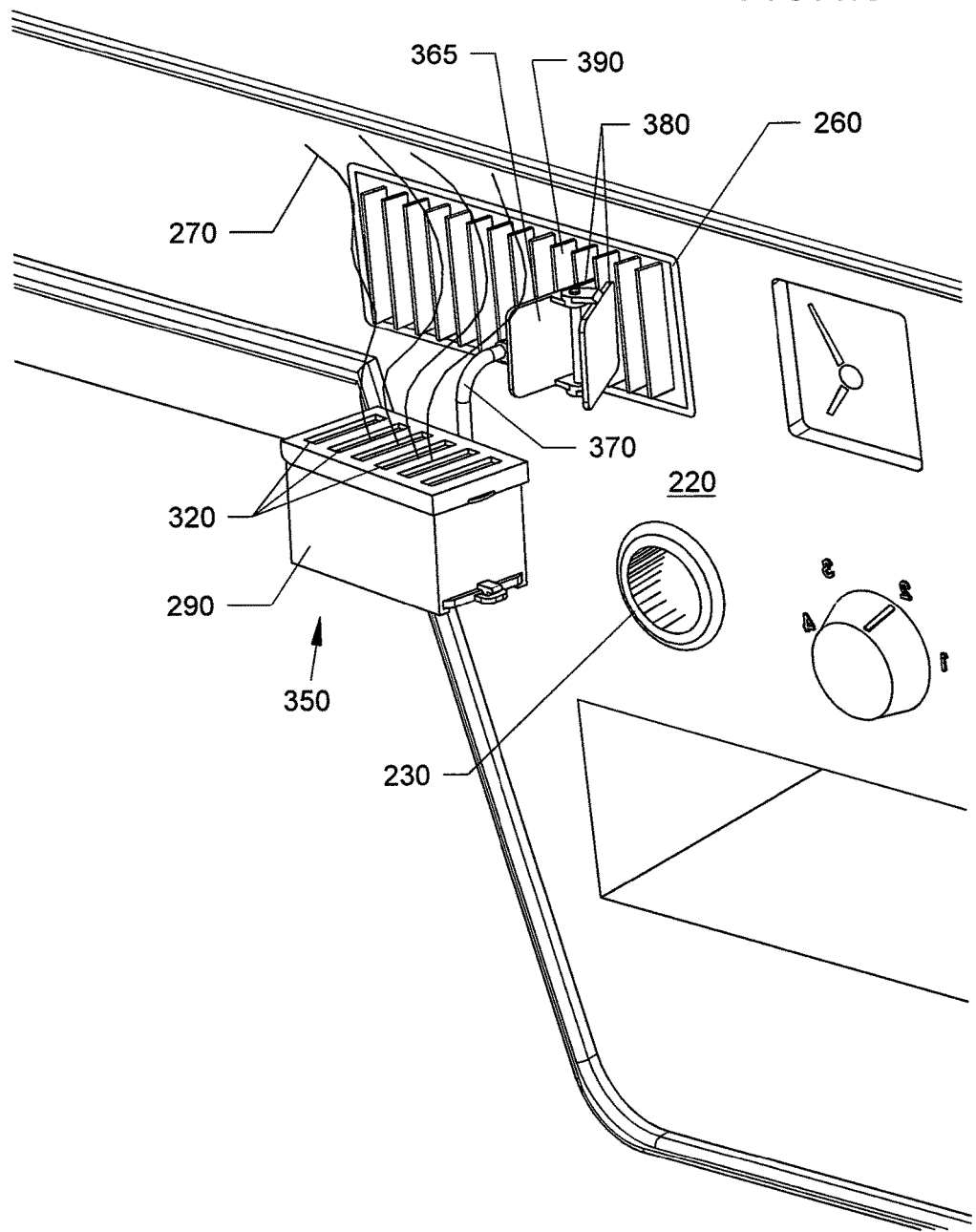
FIG. 20 is another perspective view of the clip-on style base cartridge holder of FIGS. 16-19 with holder clipped to car vent vane. The scented wax aroma is indicated. No heat is present in this assembly.

FIG. 19 is a perspective view of clip-on style basic base cartridge holder 350 of FIGS. 16-18 ready to clip to a car vent vane 390. FIG. 20 is another perspective view of the clip-on style basic base cartridge holder 350 of FIGS. 16-19 with holder clipped to car vent vane 390. The scented, pasty wax aroma is indicated at 270 and no heat is present in this assembly.

Referring to FIGS. 16-20, the basic base 360 allows for the inwardly facing rails 385 underneath the housing 315 to slide about the side edges of the basic base 360, and snaps in place with similar stop 335 and snap 330A and snap receptacle 330B. Attached to the basic base 360 can be one end of a flexible arm 370 with a second arm end attached to a spring-loaded clamp 365 that has clamp jaws 380 which can be used to clamp about a vane 390 on a vehicle air vent.

Referring to FIGS. 16-20, the cartridge 290 of scented, pasty wax can be pre-warmed/melted by the warmer/melter that was previously plugged into the vehicle accessory outlet 230.

Alternatively, the cartridge 290 can just be used to house a dispensed scented, pasty wax ribbon 75 that was not warmed, with the fragrances simply off gassing from the scented, pasty wax ribbon 75 being distributed by air coming from the vehicle air vent 260.

While the figures show the cartridge based assembly being clamped to vanes of a vehicle air vent, the cartridge based assembly can be pre-warmed and melted from an indoor electrical outlet heater style base and clamped on an air vent inside of a home or business, and the like.

Additionally, temperatures inside of vehicles during the summer months or in southern states, such as but not limited to Florida, can also cause the scented, pasty wax mixture to melt on a typical warm day, without having to use the melting devices referenced above. As such, the cartridge with sponge material can be used and clipped to and/or attached to other surfaces, and the like, without it ever having to be melted by a melter device.

Additionally, an existing heater used in a vehicle can be used as the heat source for the cartridge that is clipped to the air vent vanes. Similarly, heaters in homes and residences can be used as the heat source for the wax warmer that is clipped to the air vent vanes.

Figure 21:
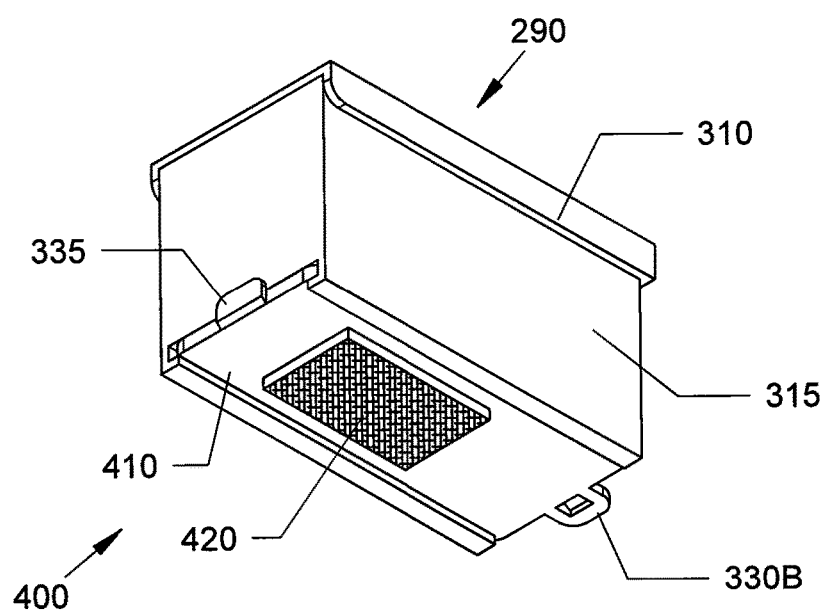
FIG. 21 is a bottom perspective view of another embodiment of an alternative mount using peel and stick tape with hook and loop fasteners.

FIG. 21 is a bottom perspective view of another embodiment 400 of the previously described cartridge assembly 290 with alternative mount on the basic base 410 without solar heater option that can use fasteners 420, such as but not limited to peel and stick tape with hook and loop fasteners, which allows the cartridge assembly 290 to be mounted to any surface that has mateable hook and loop fasteners.

FIG. 22 is a top perspective view of another embodiment of an alternative mount that illustrates how any of the previous 'basic' bases can alternately be offered with the solar heater option by expanding the height of the basic base to enclose the heater and rechargeable battery and provide the connection point for the solar panel power source 540. In the suction cup style base with solar heater option the heater is powered by a solar panel 540 with both the solar panel 540 and solar heating option suction cup style base 530 being mountable to surfaces using suction cups 450.

FIG. 23 is a bottom perspective view of the embodiment of FIG. 22.

Referring to FIGS. 22-23, a solar panel cable 570 can connect the solar panel 540 with an RCA type plug 550 that fits into RCA type jack 560. An on/off push button switch 520 can be used turn the heater base 530 on, and with a light 510, such as an LED (light emitting diode) can indicate when the heater is active. Additionally, a battery inside the heater base 530 can be charged by the solar panel 540.

Additionally, due to the low melting point of the scented, past wax mixture, the temperatures reached inside of parked vehicles during the summer months or in southern states, such as but not limited to Florida, can also be sufficient to cause the scented, pasty wax mixture to melt without ever having to use any of the melting devices referenced above. As such, the cartridge with sponge material and scented, pasty wax mixture can be used in a vehicle and clipped to and/or attached to any of the basic bases without a heater option, and clipped to the vents or attached to surfaces and the like, and without ever having to be melted by a melter device the fragrance can be refreshed daily simply by the ambient temperatures.

The scented, pasty wax mixture used in the invention has a much lower melting point, and a high fragrance output even when it is solid at room temperature. The maximum usage comes from initially melting the scented, pasty wax, mixture, and continuing to enjoying the fragrance for many hours or more after it has cooled and re-solidified. The pasty wax can be periodically remelted to 'refresh' the fragrance effect.

The term "approximately" can be +/−10% of the amount referenced. Additionally, preferred amounts and ranges can include the amounts and ranges referenced without the prefix of being approximately.

While the invention has been described, disclosed, illustrated and shown in various terms of certain embodiments or modifications which it has presumed in practice, the scope of the invention is not intended to be, nor should it be deemed to be, limited thereby, and such other modifications or embodiments as may be suggested by the teachings herein are particularly reserved especially as they fall within the breadth and scope of the claims here appended.

I claim:

1. A system for dispensing a scented, pasty wax mixture, comprising:
a flexible bag having triangular shape with a wide base open end and a narrow, closed tip end forming a funnel configuration, the flexible bag consisting of a length between approximately 12 inches and approximately 16 inches; and
a supply of scented, pasty wax mixture for filling inside of the flexible bag, the pasty wax mixture consisting of:
semi viscous petroleum derived wax consisting of between approximately 87% to approximately 94%;
fragrance oils consisting of between approximately 6% to approximately 13%; and
colors consisting of less than approximately 1%; and
a warmer for receiving a portion of the scented, pasty wax mixture being dispensed out of the opening formed in the tip end of the flexible bag, wherein the pasty wax mixture is dispensed out of an opening in the narrow lip end of the bag in a solid ribbon shape at room temperature.

2. The system of claim 1, wherein the flexible bag includes:
a clear transparent plastic or UV (ultraviolet) resistant plastic.

3. The system of claim 1, further comprising:
a tie with hole for closing off the wide base open end of the flexible bag.

4. The system of claim 1, further comprising:
a clip for closing off the narrow tip end of the flexible bag after opening.

5. The system of claim 1, wherein the narrow, closed tip end of the flexible bag includes:
a plurality of cut lines on the exterior of the bag for allowing for different amounts of the scented, pasty wax mixture to be dispensed from the flexible bag.

6. The system of claim 1, wherein the warmer includes:
a night light having a receptacle for receiving the dispensed scented, pasty wax, the night light having a plug adapted for being plugged into an electrical outlet.

7. The system of claim 6, wherein the warmer includes:
a removable cartridge for housing the receptacle; and
a clip for attaching the cartridge to an air vent grill.

8. The system of claim 6, wherein the warmer includes:
a removable cartridge for housing the receptacle; and
a mount fastener for attaching the cartridge to a surface, the mount fastener being selected from one of hook and loop fasteners, and a suction cup.

9. The system of claim 1, wherein the warmer includes:
a vehicle accessory adapter having a receptacle for receiving the dispensed scented, pasty wax mixture, the vehicle accessory adapter having a plug adapted for being plugged into a vehicle accessory electrical outlet inside of a vehicle.

10. The system of claim 9, wherein the warmer includes:
a removable cartridge for housing the receptacle; and
a clip for attaching the cartridge to a vehicle air vent inside of a vehicle.

11. The system of claim 9, wherein the warmer includes:
a removable cartridge for housing the receptacle; and
a mount fastener for attaching the cartridge to a surface, the mount fastener being selected from one of hook and loop fasteners, and a suction cup.

12. The system of claim 1, wherein the warmer includes:
a cartridge having a receptacle for receiving the dispensed scented, pasty wax mixture; and
a removable sponge for being inserted into the receptacle, wherein the sponge absorbs the portions of the scented, pasty wax mixture being melted.

13. A method for delivering scented, pasty wax mixture to a warmer, comprising the steps of:
providing a scented, pasty wax material, the pasty wax mixture consisting of:
semi viscous petroleum derived wax consisting of between approximately 87% to approximately 94%;
fragrance oils consisting of between approximately 6% to approximately 13%; and
colors consisting of less than approximately 1%;
providing a flexible bag having a wide open top end and an opposite narrow tip end, the flexible bag consisting of a length between approximately 12 inches and approximately 16 inches;
providing a candle warmer;
filling the flexible bag with the scented, pasty wax mixture;
closing the wide, open end of the filled bag;
cutting an opening in the narrow tip end of the filled bag; and
dispensing a solid ribbon shape of the scented, pasty wax mixture at room temperature from the narrow tip end opening of the filled bag onto the candle warmer.

14. The method of claim 13, wherein the step of providing the flexible bag includes the step of:
providing graduated parallel cut lines on the narrow tip end of the filled bag; and
selecting one of the graduated parallel cut lines to be cut so that a pre-determined amount of the ribbon of the scented, pasty wax mixture is dispensed from the filled bag.

15. The method of claim 13, wherein the step of providing the candle warmer includes the step of:
providing the candle warmer with a removable cartridge having a clip; and
clipping the removable cartridge to an air vent.

16. The method of claim 13, wherein the step of providing the candle warmer includes the step of:
inserting a removable sponge into the candle warmer; and
absorbing melted, scented, pasty wax mixture into the sponge when the candle warmer is turned on.

17. The system of claim 1, wherein the pasty wax consists of between approximately 87% and approximately 90%, and the fragrance oils consists of approximately 10% to approximately 13%.

18. The method of claim 13, wherein the pasty wax consists of between approximately 87% and approximately 90%, and the fragrance oils consists of approximately 10% to approximately 13%.

* * * * *